United States Patent [19]

Laing et al.

[11] 4,252,974
[45] Feb. 24, 1981

[54] CEPHALOSPORIN COMPOUNDS

[75] Inventors: Stuart B. Laing, Harrow; Gordon G. Weingarten, London, both of England

[73] Assignee: Glaxo Group Limited, London, England

[21] Appl. No.: 27,805

[22] Filed: Apr. 6, 1979

[30] Foreign Application Priority Data

Apr. 7, 1978 [GB] United Kingdom ............... 13801/78

[51] Int. Cl.³ .......................................... C07D 501/46
[52] U.S. Cl. ...................................... 544/22; 544/16; 544/21; 544/29
[58] Field of Search ...................... 544/16, 21, 29, 27, 544/28, 22

[56] References Cited

U.S. PATENT DOCUMENTS

| 3,355,452 | 11/1967 | Urech et al. | 544/16 |
| 3,875,152 | 4/1975 | Sellstedt | 544/28 |
| 3,905,963 | 9/1975 | Webber | 544/22 |
| 3,974,153 | 8/1976 | Cook et al. | 424/426 |
| 4,043,991 | 8/1977 | Hamma et al. | 544/21 |

FOREIGN PATENT DOCUMENTS 1350772 4/1974 United Kingdom .

OTHER PUBLICATIONS

Shokop et al., "Chemical Abstracts", vol. 73:14927b (1970).
Cotton et al., "Advanced Inorganic Chemistry", (1967), pp. 506–508.

Primary Examiner—Paul M. Coughlan, Jr.
Attorney, Agent, or Firm—Bacon & Thomas

[57] ABSTRACT

3-Phosphonocarbamoyloxymethyl cephalosporin compounds of formula

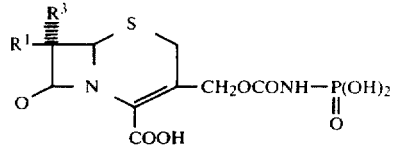

(wherein $R^1$ represents an acylamido group and $R^3$ represents hydrogen, or a lower alkyl, alkylthio or alkoxy group) and non-toxic derivatives thereof. The compounds exhibit antibiotic activity.

4 Claims, No Drawings

CEPHALOSPORIN COMPOUNDS

IMPROVEMENTS IN OR RELATING TO CEPHALOSPORIN COMPOUNDS

This invention is concerned with novel cephalosporin compounds.

The cephalosporin compounds in this specification are systematically named with reference to "cepham" after *J. Amer. Chem. Soc.*, 1962, 84, 3400; the term "cephem" refers to the basic cepham structure with one double bond.

Many cephalosporin compounds possessing a degree of antibacterial activity are known in the art. These compounds possess $\Delta^3$ unsaturation and are ordinarily substituted at the 3-position by a methyl or substituted methyl group, at the 4-position by a carboxy group, and at the $7\beta$-position by an acylamido group. In some instances the compounds may additionally be substituted at other positions, for example at the 2-position (e.g. by one or two methyl groups or a methylene group) and/or at the 7α-position (e.g. by a lower alkyl, alkoxy or alkylthio group).

Thus according to one aspect of the invention there are provided 3-phosphonocarbamoyloxymethyl cephalosporin compounds of formula

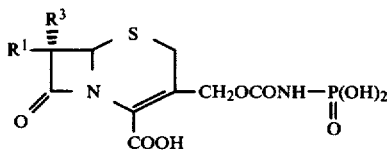

(I)

(wherein $R^1$ represents an acylamido group, conveniently one which contains 1 to 40, e.g. 1 to 25, carbon atoms, and $R^3$ represents hydrogen or a lower (e.g. $C_{1-4}$) alkyl, alkylthio or alkoxy group, e.g. a metoxy group) and non-toxic derivatives thereof.

It should be appreciated that formula (I) is a skeletal formula and is intended to embrace closely related analogues such as 2-methyl, 2-methylene and 2,2-dimethyl cephalosporins.

The term "non-toxic" as applied to the derivatives of the compounds of formula (I) of the invention means those derivatives which are physiologically acceptable in the dosages at which they are administered. Such derivatives may include, for example, salts, physiologically acceptable esters, 1-oxides and solvates, e.g. hydrates, of the compounds of formula (I), and, where appropriate, combinations thereof.

The compounds of formula (I), of the invention, including the non-toxic derivatives thereof, are characterised in vitro by antibacterial activity against a range of gram-positive and gram-negative organisms.

The properties possessed by the compounds of formula (I) according to the invention render them useful in the treatment of a variety of diseases caused by pathogenic bacteria in human beings and animals.

The compounds of formula (I) which form salts having good water-solubility are especially preferred since such salts are particularly valuable in cases where it is desired to administer high solution dosages of antibiotic, for example, in patients suffering from severe bacterial infection.

The above compounds of formula (I) are capable of forming base salts such as alkali metal, e.g. sodium or potassium, alkaline earth metal, e.g. calcium, and organic amine, e.g. procain, 1-aminoadamantane, phenylethylbenzylamine, dibenzylethylene diamine, ethanolamine, diethanolamine, triethanolamine, N-methylglucosamine and amino acid (e.g. lysine, arginine, ornithine and histidine in the d-, l- and dl-forms) salts.

A particularly preferred compound of formula (I) containing an (α-etherified oximino)-acylamido group in the 7-position is (6R,7R)-3-phosphonocarbamoyloxymethyl-7-[Z-2-(fur-2-yl)-2-methoxyiminoacetamido]-ceph-3-em-4-carboxylic acid and non-toxic derivatives thereof. In in vitro and in vivo tests which we have carried out, it was found that this compound displayed antibacterial activity which was substantially the same as that of its 3-carbamoyloxymethyl analogue which has the approved name cefuroxime and which has been found to be a valuable broad spectrum antibiotic. When administered to mice and rats by injection, the above-mentioned compound was found to be almost completely matabolised to cefuroxime. The compound thus possesses substantially the same antibacterial activity as cefuroxime in vivo and has the advantage that it can be readily converted into salts having high water-solubility. In this respect the trisodium salt of the above-mentioned compound is particularly preferred on account of its good water-solubility.

The compounds of formula I above may be prepared for example by (A) subjecting a compound of formula

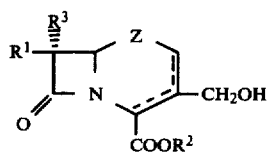

(II)

[wherein $R^1$ represents a protected amino group (e.g. an acylamido group, conveniently containing 1–40, e.g. 1 to 20 carbon atoms); $R^2$ represents hydrogen or a carboxyl blocking group e.g. the residue of an alcohol, phenol, silanol or stannanol, the residue preferably being one which may readily be split off at a later stage; $R^3$ is as defined above; Z is $>S$ or $>S\rightarrow O$ (α- or β-); and the dotted line bridging the 2-, 3- and 4-positions of the molecule indicates that the compounds are ceph-2-em or ceph-3-em compounds] to a carbamoylation reaction whereby a dihydroxyphosphoryl-carbamoyloxymethyl group is formed at the 3-position; or (B) condensing a compound of formula

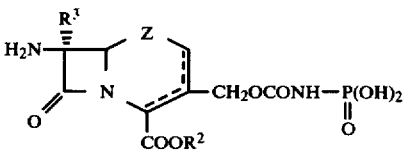

(III)

(wherein $R^2$, $R^3$, Z and the dotted line are as defined above) or a derivative thereof (e.g. an acid addition salt or N-silyl derivative or hydroxy-protected derivative thereof) with an acid corresponding to the acyl group of the acylamido group $R^1$ or a reactive derivative thereof. In the preparation of compounds of formula (I) by either of the above two methods, any of the following reactions in any appropriate sequence may, if necessary and/or desired, be carried out:

(i) conversion of a precursor for the desired acylamido group into that said group, e.g. by removal of a protecting group, (ii) conversion of a $\Delta^2$ isomer into the desired $\Delta^3$ isomer, (iii) removal of any carboxyl blocking group or any hydroxyl-protecting groups, and (iv) reduction of a cephalosporin sulphoxide product to yield the corresponding sulphide; and finally recovering the desired compound of formula (I), if necessary after separation of any isomers and if desired, after conversion of the compound to a non-toxic derivatives thereof.

Salts, particularly non-toxic salts, of the compounds of formula (I) may be formed in any convenient way, for example according to methods well known in the art. Salt formation may take place without prior isolation of the corresponding acid, by reaction with a suitable reagent e.g. an alkali metal bicarbonate or 2-ethylhexanoate.

The compounds of formula I may be prepared according to process (A) above, for example, by reacting the above compound of formula (II) with a dihalophosphinyl isocyanate, and subsequently hydrolysisng the resulting reaction product. The dihalophosphinyl isocyanate used in this process is conveniently dichlorophosphinyl isocyanate by virtue of its ready availability.

It is convenient to employ substantially equimolar amounts of the 3-hydroxymethyl cephalosporin and the dihalophosphinyl isocyanate; the use of a small excess (e.g. up to 0.5 moles) of dihalophosphinyl isocyanate may, however, be advantageous to allow for side reactions between this reagent and hydroxylic impurities (e.g. water) in the reaction system. In view of the susceptibility of dihalophosphinyl isocyanates to reaction with water, the reaction with the 3-hydroxymethyl cephalosporin is desirably conducted under anhydrous conditions; thus, for example, the reactions may be carried out under an appropriate desiccant or the reaction system may be kept dry by passage of a stream of an anhydrous inert gas such as nitrogen.

The reaction of the 3-hydroxymethyl cephalosporin compound with the dihalophosphinyl isocyanate is conveniently carried out in solution, for example, in a substantially inert organic solvent, since this facilitates control of reaction conditions such as temperature. Solvents which may be used include chlorinated hydrocarbons such as methylene chloride or 1,2-dichloroethane; ethers such as tetrahydrofuran, dioxan or diethylene glycol dimethyl ether (diglyme); esters such as ethyl acetate; ketones such as acetone and hydrocarbons such as benzene or cyclohexane. Mixtures of solvents, e.g. comprising two or more of the above-described solvents, may also be used. As indicated above, the solvent should desirably be substantially free from hydroxylic impurities to avoid unwanted side reactions involving the dihalophosphinyl isocyanate.

The temperature employed in the reaction of the 3-hydroxymethyl cephalosporin and dihalophosphinyl isocyanate may vary depending on the solvent used, but may, for example, be in the range $-50°$ to $+105°$ C., e.g. $-20°$ to $+50°$ C. The reaction is exothermic, so that cooling of the reaction system may be desirable in order to maintain a steady temperature.

The 3-hydroxymethyl cephalosporin and dihalophosphinyl isocyanate may be brought together in any convenient manner. Preferably a solution or suspension of the 3-hydroxymethyl cephalosporin may be added to the dihalophosphinyl isocyanate or a solution thereof. The dihalophosphinyl isocyanate may conveniently be formed without isolation as described in greater detail hereinafter.

The reaction may be monitored by, for example, chromatography, e.g. to determine the degree of consumption of the 3-hydroxymethyl cephalosporin.

Conversion of the 3-dihalophosphorylcarbamoyloxymethyl cephalosporin intermediate to the cephalosporin of formula (I) may be initiated by reaction with water e.g. by addition of the reaction system to water.

The hydrolysis is conveniently conducted at a pH of 10 or less, desirably at a pH of from 5 to 10, preferably 7 to 9. Since the hydrolysis is accompanied by the formation of hydrohalic acid it may be desirable to add a base to act as an acid binder. This may particularly be the case if the compound of formula (I) produced is insoluble at a low pH or if the cephalosporin contains any acid-susceptible groups.

In the hydrolysis reaction, it may be desirable to buffer the aqueous system, e.g. with sodium carbonate, sodium hydrogen carbonate, sodium acetate, sodium phosphate, calcium carbonate or calcium hydroxide, or add an acid or base such as sodium hydroxide during the course of the hydrolysis, in order to maintain the pH within the desired limits. It is generally important that the pH of the hydrolysis is not allowed to fall below values of about 5. The use of aqueous sodium hydrogen carbonate in this way has proved particularly convenient when effecting hydrolysis.

The hydrolysis may, for example, be conducted at a temperature in the range $-5°$ to $+105°$ C., e.g. $+15°$ to $+60°$ C., and may, where necessary, be monitored by, for example, chromatography.

If the compounds of general formula (I) are prepared from a starting material of formula (III), the condensation may be carried out, for example, in an analogous manner to that disclosed in British Pat. No. 1,453,049.

The above compounds of formula (III) may be prepared for example from 7-acylamido cephalosporin analogues containing a phosphonocarbamoyloxymethyl group in the 3-position, e.g. using the technique described in British Pat. No. 1,041,985, the said analogue being prepared from the corresponding 3-hydroxymethyl compound in an analogous manner to the preparation of compounds of formula (I) described above.

The compounds of formula (I) or a base salt thereof formed in the above processes, for example when a base is mixed with the reaction medium after the initial step of phosphorylation, may be isolated from the reaction mixture in conventional manner, e.g. by ion exchange, treatment with adsorption resins, gel filtration, dialysis or precipitation as an insoluble salt. The compounds of formula (I) may also be isolated as the free acid by solvent extraction from aqueous solution at low pH, e.g. at a pH below 2.

The dihalophosphinyl isocyanate employed in process (A) of the invention may readily be prepared by, for example, reaction of the appropriate phosphorus pentahalide, e.g. phosphorus pentachloride, with a carbamic acid ester, for example a lower alkyl carbamate (unless otherwise stated, the qualification "lower" is used in this specification to designate a group containing up to 8, e.g. 1 to 6 carbon atoms). The use of methyl carbamate is of particular advantage as this is an inexpensive reagent which is commercially available. The reaction may conveniently be accomplished by mixing the reagents in the presence of a diluent, e.g. dioxan, methylene chloride or 1,2-dichloroethane, and is accompanied by the formation of hydrogen halide and alkyl halide. When phosphorus pentachloride is employed as the phosphorus pentahalide this may if desired be formed in situ by interacting phosphorus trichloride and chlorine, if desired in the presence of a diluent.

Crude dihalophosphinyl isocyanates prepared by techniques such as those described above may conveniently be reacted directly, without distillation, with the 3-hydroxymethyl cephalosporin; in such cases it may be advantageous to ensure substantially complete removal of hydrogen halide from the crude dihalophosphinyl isocyanate, since the presence of hydrogen halide during carbamoylation may promote such undesirable side reactions as lactonisation of the 3-hydroxymethyl cephalosporin.

Acylamido groups which may be present at the 7-position of the cephalosporin starting materials and products in the process of the invention [e.g. as the group $R^1$ in formulae (I) and (II)] may, for example, be selected from the wide range of side chain acylamido groups known in the $\beta$-lactam antibiotic art]. It will be appreciated that where the acylamido group carries substituents such as amino, hydroxy or mercapto groups which are susceptible to reaction with dihalophosphinyl isocyanates, these substituents should be protected by substitution with an appropriate group unless such further reaction is desired in a particular instance. Thus, for example, amino groups may be protected by substitution with a mono- or divalent blocking group, suitable groups including acyl groups, for example lower alkanoyl such as acetyl, substituted lower alkanoyl, e.g. lower haloalkanoyl such as phenylacetyl and aroyl such as benzoyl or phthaloyl; lower alkoxycarbonyl groups such as ethoxycarbonyl, isobutyloxycarbonyl or t-butoxycarbonyl and substituted lower alkoxycarbonyl groups e.g. lower haloalkoxycarbonyl such as 2,2,2-trichloroethoxycarbonyl; aryl-lower alkoxycarbonyl groups such as benzyloxycarbonyl; sulphonyl groups, for example lower alkylsulphonyl such as methanesulphonyl and arylsulphonyl such as benzene sulphonyl or p-toluene sulphonyl; ylidine groups formed by reaction with an aldehyde or ketone which forms a Schiff's base, for example acetone, methylethylketone, benzaldehyde, salicylaldehyde or ethyl acetoacetate; and divalent groups such that the nitrogen atom forms part of a dihydropyridine ring (protecting groups of this last sort being obtained by, for example, reaction with formaldehyde and a $\beta$-ketoester, e.g. acetoacetic ester, as described in our Belgian Pat. No. 771,694). Hydroxyl and mercapto groups may for example, be protected by substitution with carboxylic or sulphonic acyl groups in like manner to amino groups, or, where appropriate, by etherification or thioetherification (e.g. to introduce a branched lower alkyl group such as isopropyl or t-butyl or an aralkyl group such as benzyl, benzyl substituted by one or more methoxy groups, diphenylmethyl or triphenylmethyl). The protecting groups may subsequently be removed from the cephalosporin product by methods well known in the art, for example by hydrolytic, reductive or acid-induced cleavage as appropriate.

Where the acylamido group is substituted by a carboxyl group it may also be advantageous to protect this during the course of the reaction, for example by etherification to introduce an ester group as herein described in connection with the group $R^2$.

Specific acyl groups which may be present in acylamido groups $R^1$ are illustrated in the following list, which is not intended to be exhaustive:

(i) $R^uC_nH_{2n}CO$— where $R^u$ is aryl (carbocyclic or heterocyclic), cycloalkyl, substituted aryl, substituted cycloalkyl, cycloalkadienyl, or a non-aromatic or mesionic group, and n is an integer from 1 to 4. Examples of this group include phenylacetyl wherein the phenyl group may if desired be substituted by, for example, one or more of fluoro, nitro, protected amino, protected hydroxy (e.g. esterified hydroxy such as acetoxy), methoxy, methylthio or methyl; N,N-bis (2-chloroethyl) aminophenylpropionyl; thien-2- and -3-ylacetyl; 3- and 4-isoxazolylacetyl either substituted or unsubstituted; pyridylacetyl; tetrazolylacetyl; cyclohexadienylacetyl; or a sydnoneacetyl group. Where n is other than 0, especially where n is 1, the $\alpha$-carbon atom of the acyl group may be substituted by, for example, an esterified hydroxy (e.g. acyloxy such as formyloxy or lower alkanoyloxy), etherified hydroxy (e.g. methoxy), protected amino (e.g. as hereinbefore described), carboxy, esterified carboxy, triazolyl, tetrazolyl or cyano group or a halogen atom; examples of such $\alpha$-substituted acyl groups include esterified 2-hydroxy-2-phenylacetyl, N-blocked 2-amino-2-phenyl-acetyl, 2-carboxy-2-phenylacetyl and esterified 2-carboxy-2-phenylacetyl.

(ii) $C_nH_{2n+1}CO$— where n is 0 or an integer from 1 to 7. The alkyl group may be straight or branched and, if desired may be interrupted by an oxygen or sulphur atom and/or may be substituted by, for example, a cyano group, a carboxy or esterified carboxy group (e.g. an alkoxycarbonyl group), an esterified hydroxy group, a blocked amino group or a carboxycarbonyl (—CO.COOH) or esterified carboxycarbonyl group. Examples of such groups include formyl, cyanoacetyl, butylthioacetyl, hexanoyl, heptanoyl, octanoyl, glutaroyl, esterified glutaroyl, and N-blocked (e.g. N-ethoxycarbonyl or N-benzoyl) and optionally esterified R-5-amino-5-carboxypentanoyl (e.g. R-5-benzamido-5-diphenylmethoxycarbonylpentanoyl or R-5-diphenylmethoxycarbonyl-5-isobutoxycarbonylaminopentanoyl).

(iii)

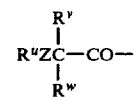

where $R^u$ has the meaning defined under (i) and in addition may be benzyl, $R^v$ and $R^w$ (which may be the same or different) each represents hydrogen, phenyl, benzyl, phenethyl or lower alkyl and Z is an oxygen or sulphur atom. Examples of such groups include phenoxyacetyl, 2-phenoxy-2-phenylacetyl, phenoxypropionyl, 2-phenoxybutyryl, benzyloxycarbonyl, 2-phenoxypropionyl, 2-phenoxybutyryl, methylthiophenoxyacetyl, phenylthioacetyl, chloro- and fluorophenylthioacetyl, pyridylthioacetyl and benzylthioacetyl.

(iv) Substituted glyoxylyl groups of the formula $R^y$.-CO.CO— where $R^y$ is an aliphatic, araliphatic or aromatic group, e.g. phenyl, thienyl or furyl or a fused benzene ring. Also included in this class are the $\alpha$-carbonyl derivatives of the above substituted glyoxylyl groups, e.g. the $\alpha$-alkoxyimino, $\alpha$-aryloxyimino and $\alpha$-acyloxyimino derivatives, especially those possessing the syn-configuration with respect to the 7-carboxamido group. Groups of this type, of which an example is the Z-2-(fur-2-yl)-2-methoxyiminoacetyl group, and which may be represented by the formula

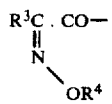

[wherein R³ represents hydrogen or an organic group (especially a carbocyclic or heterocyclic aromatic group such as phenyl, naphthyl, thienyl, thiazolyl e.g. aminothiazolyl, or furyl) and R⁴ represents hydrogen, an acyl group (e.g. a lower alkanoyl, alkenoyl, alkynoyl, haloalkanoyl, alkoxycarbonyl, haloalkoxycarbonyl, alkylthiocarbonyl or aralkyloxycarbonyl group or an aroyl or carbamoyl group) or an etherifying group (e.g. a lower alkyl, alkenyl, alkynyl, cycloalkyl, cycloalkenyl or aralkyl group or a carbocyclic or heterocyclic aryl group, or any of these groups substituted by a carboxy, esterified carboxy, aminocarbonyl or N-substituted aminocarbonyl group)], are described in greater detail in Belgian Pat. Nos. 778 630; 783 449; 801 997; 806 450; 823 651 and 843 152.

Where R² in formulae (II) and (III) represents an esterifying group this may, for example, be selected from the wide range of esterifying groups known in the cephalosporin art. A range of groups of this type, together with methods for their introduction and subsequent removal, are described in British Pat. No. 1,342,241. Representative esterifying groups thus include aryl lower alkyl groups such as p-methoxybenzyl, p-nitrobenzyl and diphenylmethyl; lower alkyl groups such as t-butyl; and lower haloalkyl groups such as 2,2,2-trichloroethyl. It will of course be appreciated that R² may represent an ester group in a compound which is to be used in medicine in which case this group should be physiologically acceptable. When such an ester group is employed it may not be necessary or desirable to effect deprotection of the carboxyl group.

Where at the end of a given preparative sequence the sulphoxide analogue of the desired compound is obtained, conversion to the corresponding sulphide may, for example, be effected by reduction of the corresponding acyloxysulphonium or alkyloxysulphonium salt prepared in situ by a known method, such as is described in British Pat. No. 1,453,049.

As also described in British Pat. No. 1,453,049 a ceph-2-em-4-carboxylic ester may be converted into a desired ceph-3-em compound by treatment of the former with a base.

The antibiotic compounds of formula (I) according to the invention may be formulated for administration in any convenient way, by analogy with other antibiotics and the invention therefore includes within its scope a pharmaceutical composition comprising a compound of formula (I) or a non-toxic derivative thereof adapted for use in human or veterinary medicine. Such compositions may be presented for use in conventional manner with the aid of any necessary pharmaceutical carriers or excipients.

The antibiotic compounds of formula (I) according to the invention may be formulated with particular advantage for injection and may be presented in unit dose form in ampoules, or in multi-dose containers with added preservative. The active ingredient may be in powder form for reconstitution with a suitable vehicle, e.g. sterile, pyrogen-free water, before use. Alternatively the compositions may take such forms as suspensions, solutions and emulsions in oily or aqueous vehicles, and may contain formulatory agents such as suspending, stabilising and/or dispersing agents.

For veterinary medicine the compositions may, for example, be formulated as intramammary preprations in either long acting or quick-release bases.

In general the compositions may contain from 0.1% upwards, e.g. 0.1–99%, preferably from 10–60% of the active material, depending on the method of administration. Where the compositions comprise dosage units, each unit will preferably contain 50–1500 mg of the active ingredient. The dosage as employed for adult human treatment will preferably range from 100–4000 mg per day, for instance 1500 mg per day, depending on the route and frequency of administration The compounds according to the invention may be administered in combination with other compatible therapeutic agents such as antibiotics, for example penicillins or other cephalosporins.

The following Examples serve to illustrate the invention. All temperatures are in °C. Thin layer chromatography (TLC) using Merck Kieselgel 60 F₂₅₄ plates, run in the solvent system indicated; detection of spots was by spraying with ninhydrin in n-butanol and heating, or by exposure to iodine vapours, or by irradiation with ultra-violet light at 254 nm. Dry solvents were used and usually contained less than 0.1% (w/v) water; the starting cephalosporins were, if necessary, dried in vacuo at 40°–50° C. and usually contained less than 1% water. The ultra-violet spectra were run in pH 6 phosphate buffer, unless otherwise specified.

The following abbreviations have been employed in the Examples:
Sodium hydrogen carbonate is represented as NaHCO₃; Magnesium sulphate as MgSO₄; phosphorus pentachloride as PCl₅; tetrahydrofuran as THF; and dimethyl sulphoxide as DMSO. Amberlite XAD-2 resin consists of a synthetic crosslinked polystyrene polymer without ionic groups attached. It is supplied in a completely hydrated state in the form of 20 to 50 mesh (that is, 0.3 to 0.5 mm diameter) beads.

EXAMPLE 1

(6R,7R)-3-Phosphonocarbamoyloxymethyl-7-[Z-2-(fur-2-yl)-2-methoxyiminoacetamido]ceph-3-em-4-carboxylic acid trisodium salt Dichlorophosphinyl isocyanate (1.76 g) was added to a solution of (6R,7R)-3-hydroxymethyl-7-[Z-2-(fur-2-yl)-2-methoxyiminoacetamido]ceph-3-em-4-carboxylic acid (3.81 g) in dioxan (50 ml) at 23°. After 5 minutes, 3% aqueous NaHCO₃ solution (135 ml) was added to adjust the pH to 5.0. After 20 minutes the solution was concentrated under reduced pressure, and then washed with ethyl acetate (4×100 ml). Freeze-drying gave a white solid (5.91 g), a portion of which (3.50 g) was dissolved in water (50 ml) and chromatographed on Amberlite XAD-2 resin [500 g, previously slurrywashed with methanol (2.5 l) and water (10 l)]. The column was eluted with water, and 75 fractions each of 25 to 30 ml were collected. Fractions 20 to 29 were combined and freeze-dried to give a white solid which was triturated with ether (50 ml) to give the title compound (0.74 g), $[\alpha]_D^{23°} +41.5°$ (c 1.03 in water); $\lambda_{max}$ 273 nm ($\epsilon$ 17 050) and $\lambda_{inf}$ 238 nm ($\epsilon$ 10 400).

EXAMPLE 2

(6R,7R)-3-Phosphonocarbamoyloxymethyl-7-[Z-2-(fur-2-yl)-2-methoxyiminoacetamido]ceph-3-em-4-carboxylic acid Dichlorophosphinyl isocyanate (5.28 g) in dioxan (20 ml) was added to a stirred suspension of (6R,7R)-3-hydroxymethyl-7-[Z-2-(fur-2-yl)-2-methoxyiminoacetamido]-ceph-3-em-4-carboxylic acid (11.44 g) in dioxan (80 ml) at 16° in a water bath; after initial addition of the isocyanate the temperature rose to 24° and eventually fell to 17°. After 10 minutes the solution was filtered under nitrogen and 1 molar aqueous NaHCO$_3$ solution (192 ml) was added to give a pH of 7.1. The solution was extracted with ethyl acetate (2×150 ml) to remove lactone impurity. Ethyl acetate (150 ml) was then added to the aqueous phase (pH 8.2) and the pH was adjusted to 0.5 by addition of concentrated hydrochloric acid. The resultant two phase suspension was separated and the aqueous suspension extracted with n-butanol (3×250 ml). Water (30 ml) was added to the butanol extract and the aqueous layer was run off. The organic phase was evaporated in vacuo to a thick slurry. Filtration of this slurry afforded a solid which was washed with ether (3×50 ml) and dried in vacuo for 20 hours to give the title compound solvated with ca 1 mole of n-butanol (5.54 g), $[\alpha]_D^{20}+45°$ (c 0.93, pH 7 phosphate buffer); $\lambda_{max}$ 273 nm (E$_{1\ cm}$1% 298).

The aqueous suspension was filtered to give a solid which was washed with n-butanol (30 ml) and ether (100 ml) and dried in vacuo to give the title compound (4.37 g), $[\alpha]_D^{21}+44°$ (c 0.96, pH 7 phosphate buffer); $\lambda_{max}$ 273 nm (E$_{1\ cm}$1% 317).

EXAMPLE 3

(6R,7R)-3-Phosphonocarbamoyloxymethyl-7-[Z-2-(fur-2-yl)-2-methoxyiminoacetamido]ceph-3-em-4-carboxylic acid trisodium salt Portions (5.04 g and 5.73 g) of the first product obtained in Example 2 were dissolved in solutions of NaHCO$_3$ (2.52 g and 2.86 g) in water (35 ml). The solutions (pH 6.7) were applied to columns containing Amberlite XAD-2 resin [1 kg. previously washed with methanol (5 liters) and water (20 liters)]. The columns were eluted with water and fractions (ca 50 ml) were collected and examined by TLC. Fractions 15 to 25 for each product were combined (pH 8.3 and 7.5) and freeze-dried to give a solid material (3.15 g and 2.80 g).

The two solids were combined, dissolved in water (50 ml) and re-chromatographed on the same column (after washing through with water (2 liters)]. Fractions (ca 50 ml) were collected and examined by TLC. Fractions 22 to 30 were combined and freeze-dried to give the title compound (1.02 g), $[\alpha]_D^{21}+41.8°$ (c 1.037, H$_2$O); $\lambda_{max}$ 275 nm (E$_{1\ cm}$1% 297).

PHARMACY EXAMPLE

Dry Powder for Injection

Sterile (6R,7R)-3-phosphonocarbamoyloxymethyl-7-[Z-2-(fur-2-yl)-2-methoxyiminoacetamido]ceph-3-em-4-carboxylic acid trisodium salt is filled into glass vials in an amount equivalent to 500 mg of the corresponding acid. The filling is effected aseptically under a blanket of sterile nitrogen. The vials are closed using rubber discs or plugs held in position by aluminium sealing rings, thereby preventing gaseous exchange or ingress of micro-organisms. The product may be reconstituted by dissolving in water or another suitable sterile vehicle shortly before administration by injection.

We claim:

1. A compound selected from the group consisting of compounds of the formula:

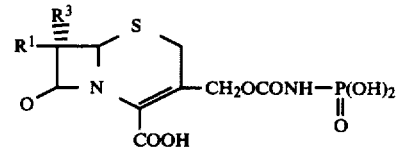

wherein R$^1$ represents an acylamido group containing from 1 to 40 carbon atoms and R$^3$ is a group selected from the group consisting of hydrogen atoms and C$_1$–C$_8$ alkyl, C$_1$–C$_8$ alkylthio and C$_1$–C$_8$ alkoxy groups and physiologically acceptable salts, esters, 1-oxides and solvates thereof.

2. The compound of claim 1 wherein R$^3$ is a hydrogen atom.

3. The compound of claim 1 which is (6R,7R)-3-phosphonocarbamoyloxymethyl-7-[Z-2-(fur-2-yl) 2-methoxyiminoacetamido]ceph-3-em-4-carboxylic acid.

4. The compound of claim 1 which is the trisodium salt of (6R,7R)-3-phosphonocarbamoyloxymethyl-7-[Z-2-(fur-2-yl)-2-methoxyiminoacetamido]-ceph-3-em-4-carboxylic acid.

* * * * *